(12) United States Patent
Monstadt et al.

(10) Patent No.: US 10,292,803 B2
(45) Date of Patent: *May 21, 2019

(54) THROMBECTOMY DEVICE

(75) Inventors: Hermann Monstadt, Bochum (DE); Ralf Hannes, Dortmund (DE); Jörg Ascherfeld, Hattingen (DE)

(73) Assignee: phenox GmbH, Bochum (DE)

( * ) Notice: Subject to any disclaimer, the term of this patent is extended or adjusted under 35 U.S.C. 154(b) by 742 days.

This patent is subject to a terminal disclaimer.

(21) Appl. No.: 14/117,553

(22) PCT Filed: May 14, 2012

(86) PCT No.: PCT/EP2012/002060
§ 371 (c)(1),
(2), (4) Date: Aug. 7, 2014

(87) PCT Pub. No.: WO2012/156069
PCT Pub. Date: Nov. 22, 2012

(65) Prior Publication Data
US 2014/0343595 A1    Nov. 20, 2014

(30) Foreign Application Priority Data

May 13, 2011 (DE) .................. 10 2011 101 522

(51) Int. Cl.
*A61M 29/00* (2006.01)
*A61F 2/01* (2006.01)
*A61B 17/221* (2006.01)
*A61F 2/91* (2013.01)
*A61B 17/22* (2006.01)
*A61B 17/00* (2006.01)
*A61F 2/95* (2013.01)

(52) U.S. Cl.
CPC .............. *A61F 2/01* (2013.01); *A61B 17/221* (2013.01); *A61F 2/91* (2013.01);
(Continued)

(58) Field of Classification Search
CPC ............ A61B 17/221; A61B 17/12113; A61B 2017/00867; A61B 2017/22038;
(Continued)

(56) References Cited

U.S. PATENT DOCUMENTS 5,618,299 A    4/1997  Khosravi et al.
6,290,720 B1 *  9/2001 Khosravi .................. A61F 2/07
                                                    623/1.13
(Continued)

FOREIGN PATENT DOCUMENTS

WO      2009105710 A1    8/2009
WO   WO 2009105710 A1 *  8/2009 ........... A61B 17/221

OTHER PUBLICATIONS

Aug. 3, 2015 Office Action in related U.S. Appl. No. 13/885,514.
Office Action dated Oct. 5, 2016 issued in connection With U.S. Appl. No. 13/885,514.

*Primary Examiner* — Robert A Lynch
*Assistant Examiner* — Mohamed G Gabr
(74) *Attorney, Agent, or Firm* — Brooks Kushman P.C.

(57) ABSTRACT

The invention relates to a thrombectomy device with a substantially cylindrical stent structure (1), which has a multiplicity of meshes (3, 4) and two connectors (5, 5') that are arranged on different meshes (3) at the proximal end of the stent structure (1), and with a guide wire (12), which has a coupling element (11) to which the connectors (5, 5') are coupled, with a slit (7), which extends in a helical formation across the jacket surface (8) of the stent structure (1), and with a tensioning bow (9), which spans the slit (7) at the proximal end.

12 Claims, 4 Drawing Sheets

(52) U.S. Cl.
CPC ............... *A61B 2017/00867* (2013.01); *A61B 2017/2215* (2013.01); *A61B 2017/22038* (2013.01); *A61F 2002/9505* (2013.01); *A61F 2002/9528* (2013.01); *A61F 2002/9534* (2013.01); *A61F 2230/0019* (2013.01); *A61F 2230/0026* (2013.01)

(58) Field of Classification Search
CPC ..... A61B 2017/2215; A61F 2002/9528; A61F 2002/9534; A61F 2002/823; A61F 2002/9505; A61F 2230/0019; A61F 2230/0026; A61F 2/01; A61F 2/91; A61F 2/90; A61F 2/915; A61F 2/856
USPC ......................................................... 606/200
See application file for complete search history.

(56) References Cited

U.S. PATENT DOCUMENTS

| | | | |
|---|---|---|---|
| 6,425,915 | B1 | 7/2002 | Khosravi et al. |
| 8,945,161 | B2 | 2/2015 | Miloslavski et al. |
| 9,034,026 | B2 | 5/2015 | Hannes et al. |
| 9,107,670 | B2 | 8/2015 | Hannes et al. |
| 2003/0100917 | A1* | 5/2003 | Boyle .................... A61F 2/013 606/200 |
| 2005/0209678 | A1 | 9/2005 | Henkes et al. |
| 2009/0198269 | A1 | 8/2009 | Hannes et al. |
| 2009/0292297 | A1 | 11/2009 | Ferrere |
| 2009/0306702 | A1 | 12/2009 | Miloslavski et al. |
| 2010/0152834 | A1 | 6/2010 | Hannes et al. |
| 2011/0009875 | A1* | 1/2011 | Grandfield ............ A61B 17/221 606/127 |
| 2011/0009940 | A1* | 1/2011 | Grandfield ................ A61F 2/90 623/1.11 |
| 2011/0060359 | A1 | 3/2011 | Hannes et al. |
| 2011/0184451 | A1 | 7/2011 | Sahl |
| 2011/0238148 | A1 | 9/2011 | Monstadt et al. |
| 2011/0264193 | A1* | 10/2011 | Abunassar .............. A61F 2/915 623/1.15 |
| 2013/0138198 | A1 | 5/2013 | Aporta et al. |
| 2013/0211492 | A1 | 8/2013 | Schneider et al. |
| 2013/0296916 | A1 | 11/2013 | Monstadt et al. |
| 2014/0058420 | A1 | 2/2014 | Hannes et al. |
| 2014/0058498 | A1 | 2/2014 | Hannes et al. |

* cited by examiner

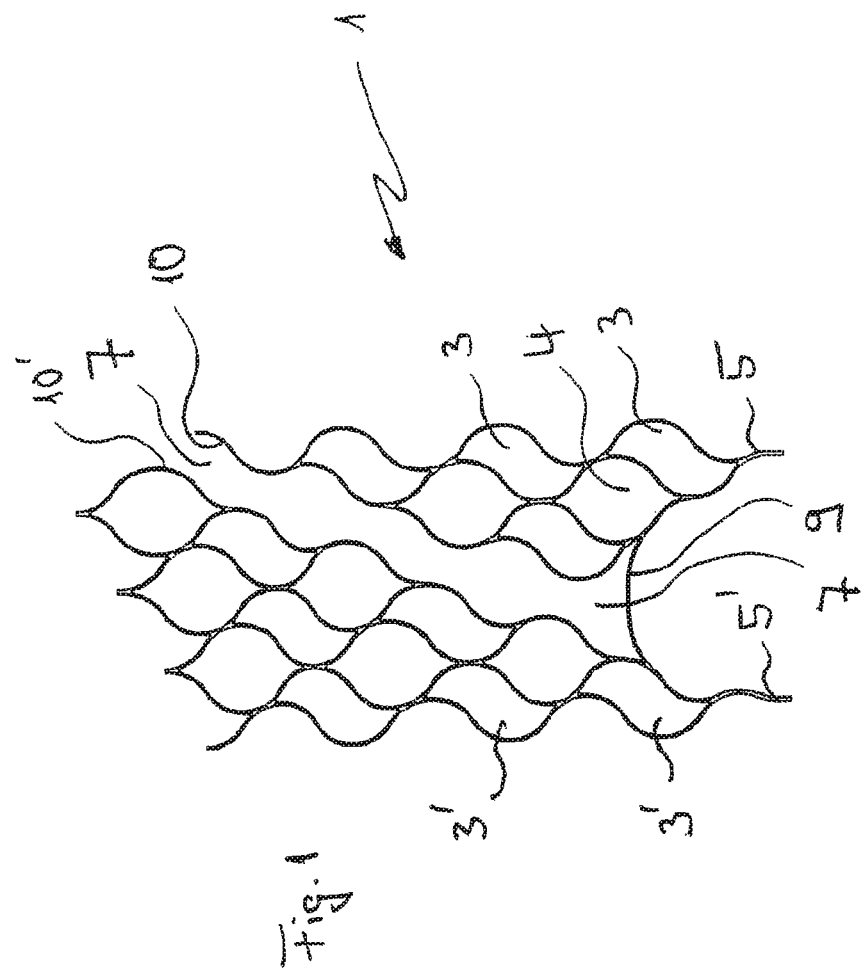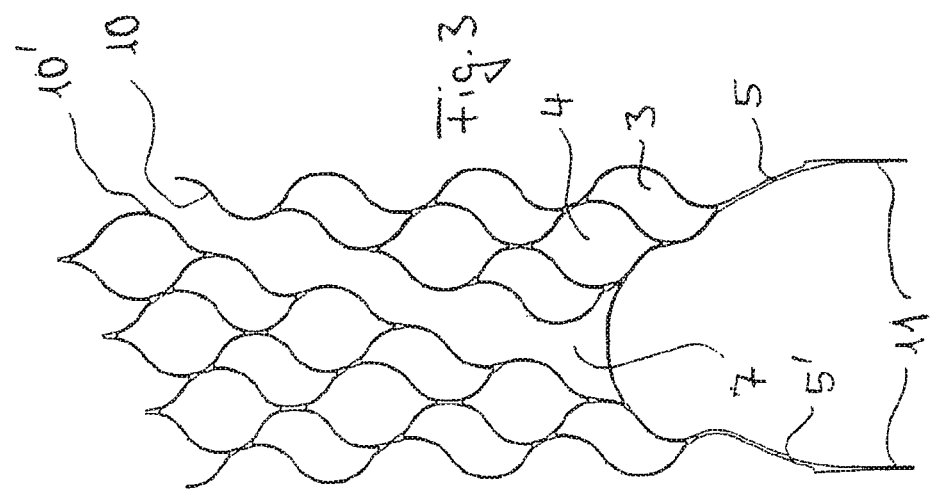

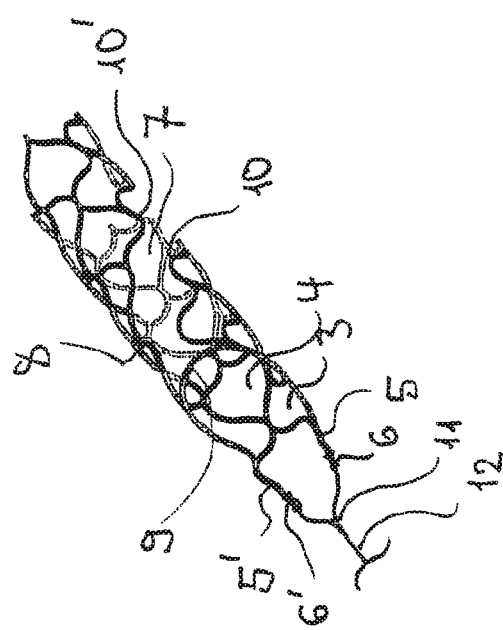
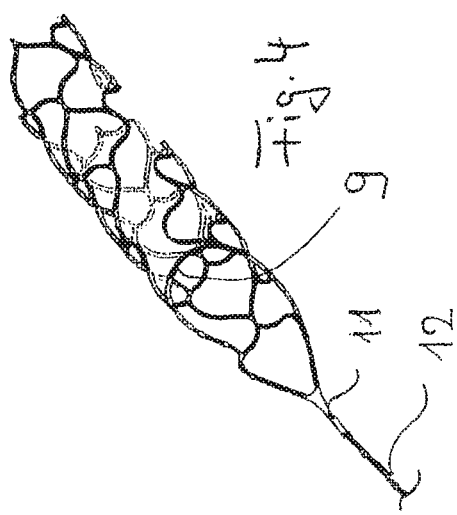

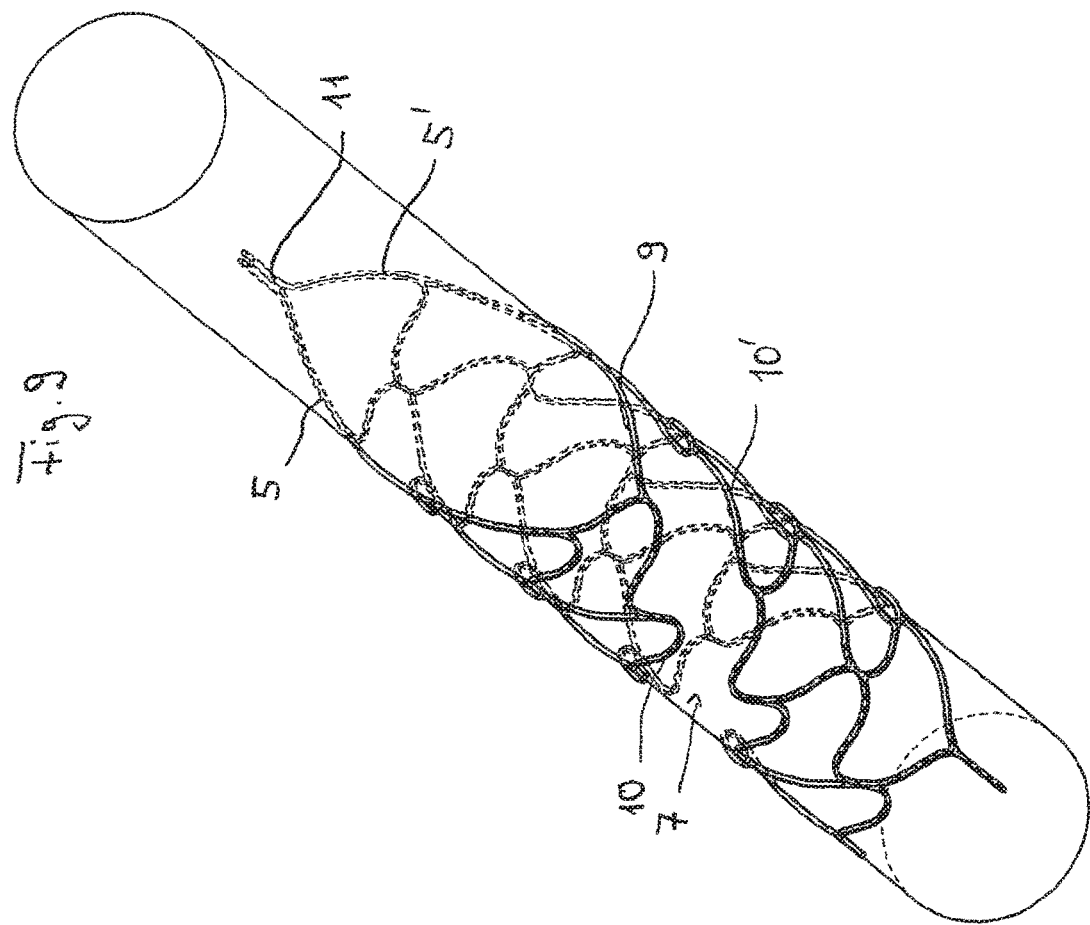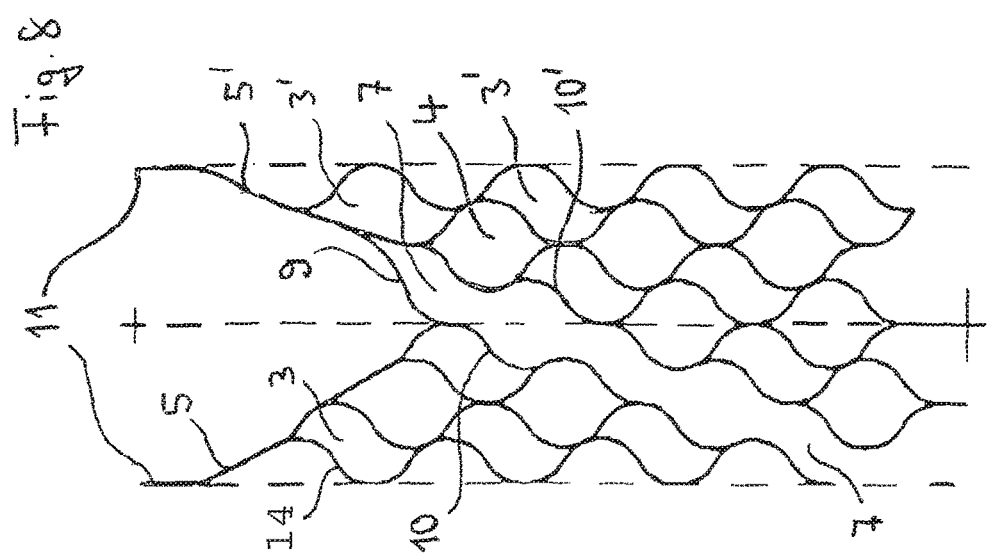

THROMBECTOMY DEVICE

The invention relates to a thrombectomy device having an essentially cylindrical stent structure comprising a plurality of meshes as well as two connectors arranged at various meshes at the proximal end of the stent structure, and a guidewire provided with a coupling element to which the connectors are attached. In particular, the thrombectomy device is intended to remove, for the patient in a gentle and reliable manner, clots/thrombi occurring in the cerebral area as they are frequently encountered during apoplectic strokes.

Thromboembolic diseases such as cardiac infarction, pulmonary embolism, peripheral thrombosis, organ embolisms etc. are typically caused by a thromboembolism (hereinafter for short clot or thrombus), i.e. a visco-elastic blood clot comprising platelets, fibrinogen, coagulation factors etc. forming in a blood vessel which it obstructs either wholly or in part. The obstruction of organ arteries also leads to the supply of oxygen and nutrients to the associated tissue being interrupted. The disorder of the functional metabolism linked with functional losses is closely followed by a failure of the structural metabolism resulting in the relevant tissue becoming destroyed (infarction). Organs most frequently affected in this way are the heart and the brain. Nevertheless, the arteries of the limbs as well as pulmonary arteries are also impaired. Venous thromboses and thromboembolic occlusions are frequently occurring in the leg and pelvic veins as well. The disease pattern of a thrombotic occlusion of an intracranial sinus may lead to severe intracerebral hemorrhage due to a failure of venous drainage of brain tissue.

In view of the severity of the disease patterns associated with thromboembolism and the prevalence rate of such diseases various techniques are known which are aimed at dissolving or removing clots/thrombi.

It is known in this context to treat such patients with thrombolytic agents such as streptokinase or urokinase or anticoagulants intended to achieve thrombolysis or limit the clot growth. Since treatment methods of this kind are usually very time consuming they are frequently combined with invasions aimed at reducing the size of or removing the clot or embolus mechanically.

Aside from open surgical operations prior art techniques more and more embrace the use of transluminal or endovascular, catheter-guided interventional therapy methods because these are of less invasive nature. It is thus known to remove the clot from the patient's body by means of vacuum producing suction catheters or mechanically using catheters provided with capturing cages, coils, hooks or similar elements; refer to U.S. Pat. No. 6,245,089 B1, U.S. Pat. No. 5,171,233 A1, Thomas E. Mayer et al., Stroke 2002 (9), 2232.

Drawbacks associated with thrombolytic treatment methods are that they seldom bring success after relevant time frame requirements have expired. Also the known transluminal devices often fail to remove the clot completely and, moreover, there is a risk of the clot or fragments thereof being released into the blood stream thus passing on to vessels of smaller lumen where they may only be reached or treated with difficulty. Furthermore, due to their size and/or low flexibility the devices known from prior art are only inadequately suited for the removal of clots from greatly convoluted vessels or those of particularly small lumen such as those in the brain.

From publication WO 2004/008991 A1 a medical implant is known that is designed in the form of an open stent and intended for the treatment of aneurysms and other vascular malformations. Via a guidewire this implant is transferred to the application site and released there. It was proposed to employ this combination of implant and guidewire for the extraction of clots which necessitated, however, to refrain from detaching the implant element from the guidewire. However, disadvantage of this configuration is that tensioning or spring forces are relatively low. The shearing effect this device exerts on the clot located in the wall of the vessel is not always sufficient so that clot remnants are left in the vessel. The attachment method to the guidewire via a tapering structure (teardrop shape) results, in particular, in the proximal area of the structure becoming more slim or slender under tension which impairs the efficiency of the device.

In view of the disadvantages linked with prior-art technology it is therefore the objective of the present invention to provide a device for the extraction of foreign objects and clots out of blood vessels, said device especially allowing the removal of clots from vessels of small lumen, being well maneuverable in greatly convoluted vessels, and having a large effective surface/area.

According to the invention this objective is reached by proposing a device of the kind first mentioned above that is provided with a slot extending helically over the generated surface of the stent structure, with a retaining clip spanning said slot at the proximal end of the stent structure.

The device according to the invention consists of a cylindrical structure as it is used for stents, with said structure having a plurality of meshes. Via two connectors said structure is attached to a guidewire which enables the structure to be accurately placed. At the proximal end the connectors are arranged in a mesh structure and terminate in a coupling element constituting the distal end of the guidewire.

The term "proximal" as it is used here denotes the end or side nearest to the attending physician whereas the "distal" end or side faces away from the physician, for example of the stent structure or the guidewire.

The mesh structure of the stent may be provided in the form of a braided structure, i.e. consisting of individual wires, but should preferably be a cut structure for which a tube of suitable diameter is used out of which the mesh structure is cut by means of a laser. The material is usually a metal, however plastic material may be employed as well. The elasticity of the material must be sufficient to enable a contraction to suit the diameter of a customary catheter and, moreover, bring about the expansion to assume the desired and prescribed diameter when liberated from the catheter.

Apart from iron alloys (stainless steel, spring steel) and cobalt-chromium alloys especially shape memory alloys are suited for use as stent material, for example binary titanium-nickel alloys (Nitinol) and ternary nickel-titanium-chromium alloys (chromium-doped alloys). Nitinol in particular is known for application in self-expanding stent structures in the neurovascular field.

The inventive device is basically a flat/planar structure rolled up to form a tubular object which is provided with a slot extending over the generated surface of the stent structure in a coiled or helical fashion. This slot may extend to form a complete coil/helix of 360° but may also be arranged to just form a partial coil/helix of 180° or 120° for example. The generated surface of the stent structure is open in the area of said slot with the width of the slot at the place of application also being determined by the lumen of the vessel since the structure of the stent when released from the catheter is capable of unfolding only to such an extent as the vessel lumen permits.

To fix the stent structure in position and also bring a certain amount of tension to bear on the structure a retaining clip is used to span the slot at the proximal end of the stent structure. This retaining clip increases the radial force of the self-expanding structure and, moreover, serves to keep the oppositely arranged edges of the stent structure alongside the slot in position relative to each other.

In addition to the retaining clip arranged at the proximal end the inventive thrombectomy device may also be provided with more retaining clips to be located in the central and distal area. However, in the event shape memory materials capable of exhibiting an adequate shape recovery effect are employed retaining clips may be dispensed with altogether.

Application of the inventive thrombectomy device requires its transfer by means of a catheter to the application site where it is released from the catheter either within the clot itself or at a location distally of the clot. The device expands within the vessel and adapts to the vessel lumen. As soon as the device unfolds or when it is retracted the clot material is captured in the mesh structure and carried along when the device is drawn back into the catheter. Fragments of the clot still adhering to the wall of the vessel are removed and entrained by the shearing action carried out by the mesh and along the edges of the slot. The clot is drawn into the catheter and extracted from the body when the catheter is removed.

For the extraction of the clot the helical configuration of the slot over the generated surface offers special advantages in that the edges of the stent structure alongside the slot move tangentially along the circumference of the wall of the vessel. This improves the shearing effect. Moreover, the helical or coiled extension of the slot also improves (reduces) the bending stiffness in such a way that the device can better adapt to tortuous vessel patterns. This not only facilitates placement of the device but also the extraction of clots from complex vessel structures.

The proximally arranged clip enhances the radial forces the stent structure exerts in the proximal area. In particular, the provision of this clip not only reduces slimming of the stent structure but also the tensile stresses as they occur when the device is retracted into the catheter. At the same time an additional peeling effect is brought about same as achieved with the meshes and edges of the stent structure.

However, of special significance is that the unfolding force in the proximal zone is improved which enables the stent structure to be optimally adapted to the vessel lumen. At the same time this arrangement prevents the stent areas which are separated by the slot from being displaced relative to each other.

To enable the stent structure with clip to be easily retracted into the catheter the retaining clip is arranged so as to point towards the distal end of the stent structure. This means the curved portion of the clip is closed distally while at the proximal end and together with the connectors it forms a loop which terminates in the coupling element, similar to the opening in a capturing basket.

Alternatively, the retaining clip spans the slot in the stent structure in a wave-like fashion, for example in a manner that the clip takes up and continues the contour of the mesh structure edges from one side of the slot to the other.

In accordance with a variant of the invention the inventive stent structure may be closed off at the distal end by means of a mesh structure with a view to collecting thrombotic material as if using a capturing basket.

As mentioned earlier, the stent structure according to the invention is preferably cut out of a cylindrical tube with the help of a laser. Using this method the individual meshes can be provided with a special cross section, for example a square, rectangular or trapezoidal one. In the case of rectangular and trapezoidal shapes either the narrow or small side of the cross section can be arranged on the outer surface or the long side. It is preferred, however, that the narrow side of both the rectangular shape and, in particular, the trapezoidal shape faces the vessel wall which enables the clot to penetrate into the mesh structure more easily and allows the clot mass to be effectively displaced when the stent structure expands.

The connectors located at the proximal end of the stent structure lead from the proximal honeycombs adjoining the slot to a coupling element to which the honeycombs are attached and in which they terminate. They are part of the stent structure and for that reason consist of the same material.

The guidewire of the thrombectomy device according to the invention is of customary make as it is commonly used for endovascular purposes and especially in the field of neuroradiology. Distally, it terminates in the coupling element to which the proximal ends of the connectors are attached.

The coupling element itself may be a simple spot weld where guidewire and connector converge and terminate. However, the coupling element may also be of customary design allowing the liberation of the cylindrical stent structure whenever necessary, especially if a retrieval is not desirable or inappropriate for medical reasons because such a retrieval would result in impairing the patient. In such a case the stent structure can remain in the body as a stent and be effectively put to use in that it forms out a duct or channel within the clot with the mesh structure causing the clot to be pressed against the vessel wall.

In the latter case, for example, the coupling element is a mechanical one suitably designed to permit the connectors being released when exiting the catheter. Numerous systems of this nature have been described in technical literature, likewise hydraulic disconnecting systems. Especially suited are electrolytic detachment systems in which an electrolytically corrodible part is dissolved by applying electrical energy resulting in the connection between stent structure and guidewire being severed. As per a first variant the coupling element may be designed as such an electrolytically dissolvable part whereas a second variant provides for the connectors being equipped with such a detachment point or a separate detachment element which dissolves when electrical current is applied. Suitable detachment elements are pre-corroded stainless steel elements, magnesium elements or cobalt-chromium alloys. Such systems have been described in literature.

For the design of the proximal area of the cylindrical stent structure preferably short connectors are to be provided. The distance between the proximal end of the mesh structure and the coupling element shall be kept short to reduce, on the one hand, the unused device length and moreover increase the tension in the capturing sling formed with the retaining clip at the proximal end of the structure. As proposed by a special embodiment of the invention the distal area of the cylindrical stent structure may be enlarged in a cone- or trumpet-shaped fashion to enable this area of the device to be well adapted to the vessel lumen. To effectively remove clots/thrombi from a vessel the effective area of the device must be as large as possible so that the surface of the device has optimal contact with the vessel wall. The larger the contact surface the higher the chances of eliminating the clot completely.

Guidewire and/or stent structure may be provided in the usual way with radiopaque markers, for example in the form of spirals or sleeves.

Further elucidation of the invention is provided through the enclosed figures by way of examples, where FIG. 1 is a planar representation of a first variant of the inventive stent structure;

FIG. 2 is a spatial representation of the stent structure shown in FIG. 1;

FIG. 3 is a planar representation of a second variant of an inventive stent structure;

FIG. 4 illustrates a spatial representation of the stent structure shown in FIG. 3 with attached guidewire;

FIG. 8 is a planar view of another embodiment and

FIG. 9 is a spatial representation of the stent structure shown in FIG. 8.

Figure 5:
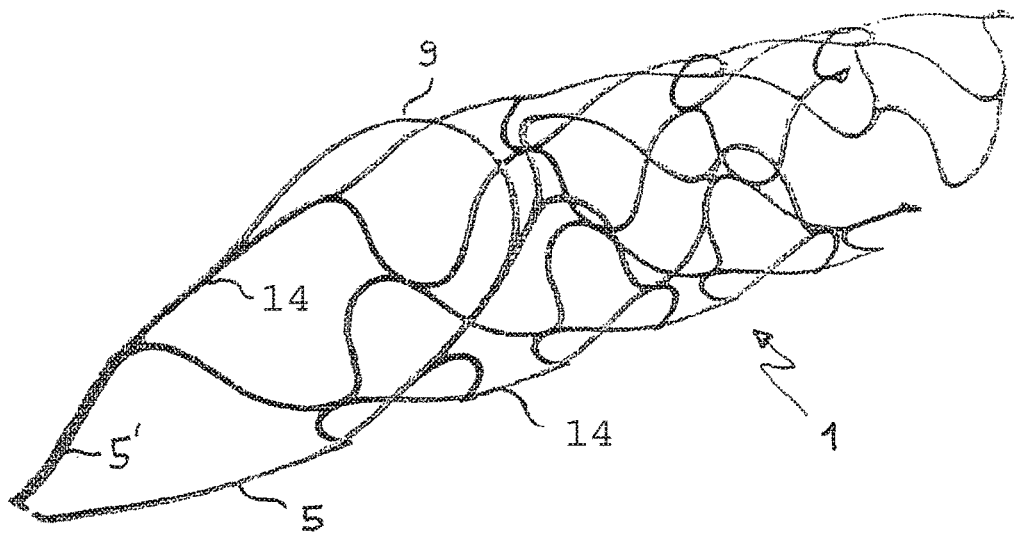
FIG. 5 is a perspective view of an inventive stent structure with two connectors.

FIGS. 1 and 3 show two variants of an inventive cylindrical stent structure 1 illustrating individual meshes 3 and 4 and connectors 5 and 5'. Meshes 3 and 4 are of different shape, with mesh type (3) having a wave-like form and mesh type (4) a more rounded form with two tips. These two interacting mesh types/shapes lend stability as well as flexibility to the overall device structure.

In the planar representations of FIGS. 1 and 3 a slot or duct 7 extends through the stent structure, said slot being spanned by retaining clip 9 at the proximal end of the structure. Slot 7 is delimited by edges 10 and 10' of the mesh structure. Slot 7 does not run parallelly to the longitudinal axis of the structure but obliquely to it so that in a spatial representation the slot progresses in a helical configuration along the generated surface of the device (see FIG. 2/4).

FIGS. 1 and 3 show a planar representation of the cut-apart stent structure 1; the spatial representations are shown in FIGS. 2 and 4. As can be seen from the planar representation meshes 3 abut directly against meshes 3' in such a manner that an all in all tubular object is formed with a slot or duct 7 extending around roughly half of the generated surface 8.

The variants illustrated in FIGS. 1 and 3 differ as far as the form of connectors 5 and 5' are concerned which in the case of FIG. 3 are of greater length and attached to a coupling element 11 (see FIG. 4). The coupling element 11 may, for example, be of electrolytically corrodible type, i.e. a system that enables the stent structure 1 to be detached from guidewire 12 (see FIG. 4). In the variant depicted in FIG. 2 two detachment or severance elements 6, 6' may be provided for the purpose of disconnecting the device electrolytically.

Common to both embodiments is that slot 7 is spanned by retaining clip 9. The retaining clip 9 is attached to the edges 10, 10' of the honeycombs of the mesh construct with the clip curvature pointing towards the distal side of the stent structure. This enables the stent structure to be retracted into a catheter without problems. Together with the adjoining connectors 5 and 5' the retaining clip 9 forms a capturing loop or opening of a capturing basket terminating in the coupling element 11 (FIG. 4). Moreover, the distal end of the stent structure may be closed off by means of a mesh structure.

In FIGS. 2 and 4 which illustrate the stent structures of FIGS. 1 and 3 in the form of a spatial representation the strands of the stent structure that are located at the rear are shown in light color. It is noticeable from the figures that at the proximal end of the structure slot 7 is located that passes under retaining clip 9 and extends in a helical fashion to the right around the generated surface 8 of the stent structure. Distally, slot 7 ends at the underside of the stent structure 1 and thus has performed a turn of approximately 180°.

FIG. 5 is a spatial representation of an inventive stent structure with connectors 5 and 5' being provided with inwardly pointing hooks arranged with a view to engaging with a suitably designed receiving portion of a coupling element 11 of a guidewire 12. As long as the coupling element accommodating the proximal end of the connectors 5 and 5' is situated inside a catheter the stent structure 1 remains connected to the guidewire. When the device is pushed out of the catheter said link between connectors 5, 5' and coupling element 11 is broken so that the structure is released to function as stent remaining in the vascular system. However, such a disconnection will only take place in special (emergency) cases, for instance if the device cannot be retracted into the catheter readily or without causing problems.

Clearly visible in FIG. 5 is the loop structure formed by retaining clip 9 and connectors 5, 5' as well as the arrangement of strands 14 of the stent structure over generated surface 8, with edges of said strands serving to act on the clot material to be removed by shearing it off the vessel wall.

Figure 6:
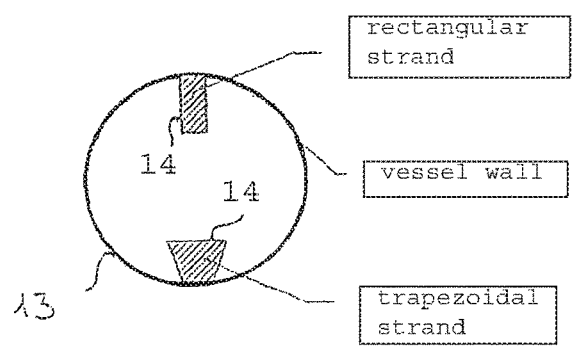
FIG. 6 is a representation of the cross sections of the stent structure strands.

FIG. 6 shows the two preferred embodiments of strands 14 having a rectangular and a trapezoidal cross section, with the narrow or small side of the strands pointing in both cases towards the generated surface 8 of the stent structure 1, and thus, respectively, to the wall of the vessel 13. These design variants ensure that the meshing not only has the desired stability but also exerts a good shearing and displacement effect on the clot.

Figure 7:
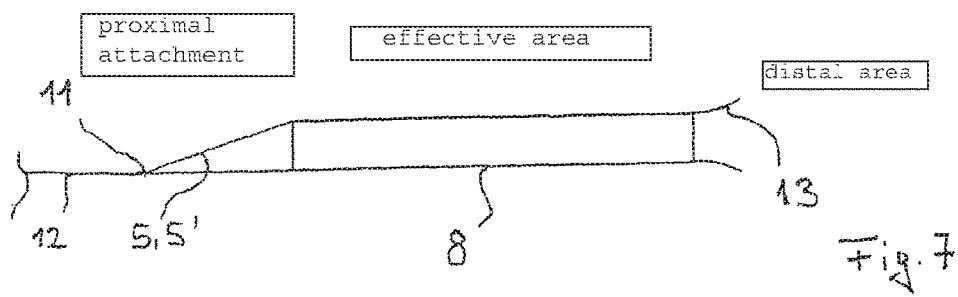
FIG. 7 is a schematic view of the inventive thrombectomy device.

FIG. 7 shows as a schematic representation the buildup of an inventive thrombectomy device comprising the guidewire 12, coupling element 11, the area of the proximal attachment with connectors 5, 5', the effective area with generated surface 8 as well as the distal area 13 having a trumpet-shaped enlargement.

FIG. 8 shows another embodiment of a thrombectomy device according to the invention that essentially coincides with the respective device as per FIG. 1. In comparison to the latter there is a differently designed retaining clip 9 that proximally spans or bridges the slot 7. The retaining clip 9 in this case has a wave-like configuration and is attached to the lateral surface or edge of the mesh structure 10 from where it passes over to the oppositely arranged edge 10' thus continuing the wave-like mesh contour. The connectors 5, 5' with adjoining mesh edges and the retaining clip 9 jointly form a kind of loop similar to the opening of a capturing basket which facilitates retracting the thrombectomy device into a catheter and moreover is suited to shear off clots or clot remnants adhering to the wall of a vessel.

It is to be understood that FIG. 8, same as FIGS. 1 and 2, illustrates the inventive device cut apart, i.e. is a planar representation. Nevertheless, the device actually has of course a spatial tubular form as shown in FIG. 9 which shows it integrated in a tube.

FIG. 9 is a spatial view of the thrombectomy device illustrated in FIG. 8 wherein the strands and meshes located at the front side are shown as solid lines and those at the rear side as dashed lines. The two connectors 5 and 5' join and terminate in coupling element 11 and together with the adjoining mesh edges and the retaining clip 9 form the "capturing basket" as described herein-before. The figure indicates the helical configuration and extension of slot 7. Slot 7 is delimited by mesh edges 10 and 10' and spanned by the retaining clip 9.

In the drawings identical reference numerals are meant to refer to the same subject matter.

The invention claimed is:

1. Thrombectomy device with
   an essentially cylindrical stent structure (1) having a plurality of meshes (3, 4) generating a surface (8) as well as two connectors (5, 5') arranged at different meshes (3, 3') of the plurality of meshes (3,4) at the proximal end of the stent structure (1), and
   a guidewire (12) provided with a coupling element (11) arranged proximally to which the connectors (5, 5') are attached,
   wherein the stent structure is characterized by a continuous slot (7) open at a distal end thereof and extending in a helical or coiled fashion over and throughout the length of the generated surface (8) of the stent structure (1), and a retaining clip (9) spanning the slot (7) in a wave-like manner at the proximal end of the stent structure (1),
   the retaining clip (9) being attached to rims (10, 10') of the stent structure (1),
   wherein the retaining clip (9) forms an arch that points to the distal end of the stent structure (9), and
   wherein the retaining clip (9) and the connectors (5, 5') form a loop that terminates in the coupling element (11).

2. Device according to claim 1, characterized in that the stent structure comprises a shape memory material.

3. The device of claim 2, wherein the shape memory material is Nitinol or a nickel-titanium-chromium alloy.

4. Device according to claim 1, characterized in that said device is provided with one or several additional retaining clips (9) arranged in the central and/or distal portion of the stent structure (1).

5. Device according to claim 1, characterized in that the stent structure (1) is cut out of a tube and provided with strands having rectangular or trapezoidal cross sections.

6. Device according to claim 5, characterized in that the stent structure (1) has a generated surface (8) formed by a narrow or small side of the strand cross sections.

7. Device according to claim 1, characterized in that the stent structure (1) can be detached from the guidewire (12) mechanically, hydraulically, or electrochemically.

8. Device according to claim 7, characterized in that the coupling element (11) is designed as detachment or severance element.

9. Device according to claim 7, characterized by two detachment locations.

10. The device of claim 9, wherein the detachment locations have electrochemical detachment characteristics.

11. Device according to claim 1, characterized in that the distal end of the stent structure (1) has a cone- or trumpet-shaped enlargement.

12. Device according to claim 1, characterized by marker elements.

* * * * *